United States Patent [19]

John

[11] 4,201,224
[45] May 6, 1980

[54] ELECTROENCEPHALOGRAPHIC METHOD AND SYSTEM FOR THE QUANTITATIVE DESCRIPTION OF PATIENT BRAIN STATES

[76] Inventor: E. Roy John, 930 Greacen La., Mamaroneck, N.Y. 10546

[21] Appl. No.: 974,445

[22] Filed: Dec. 29, 1978

[51] Int. Cl.² .............................................. A61B 5/04
[52] U.S. Cl. ..................................................... 128/731
[58] Field of Search ................ 128/731, 712, 710, 699

[56] References Cited

U.S. PATENT DOCUMENTS

| | | | |
|---|---|---|---|
| 3,809,069 | 5/1974 | Bennett | 128/731 |
| 3,893,450 | 7/1975 | Ertl | 128/731 |
| 3,901,215 | 8/1975 | John | 128/731 |
| 4,092,981 | 6/1978 | Ertl | 128/731 |

Primary Examiner—William E. Kamm
Attorney, Agent, or Firm—Eliot S. Gerber

[57] ABSTRACT

A method and system for the quantitative description of human abnormal brain states, for example, to distinguish cerebral death from a barbiturate induced deep coma, includes an electroencephalograph (EEG) system utilizing scalp electrodes and amplifiers. A computer based system controls a multimodal stimulator (clicks, flashes, etc.) to provide evoked response data for different sensory systems. The ongoing EEG and averaged response data are processed quantitatively and compared with previously stored normative data, describing brain states in patients free of head trauma, to calculate a set of Z-transformations. The Z-transformations define $\bar{Z}$, the brain state vector (BSV), which may be visually displayed. The length, direction and change of BSV over time provide an evaluation of the anatomical location of any damage, the severity of functional impairment and the rate of improvement or deterioration of the patient's state in order to aid in selection and guidance of treatment.

23 Claims, 2 Drawing Figures

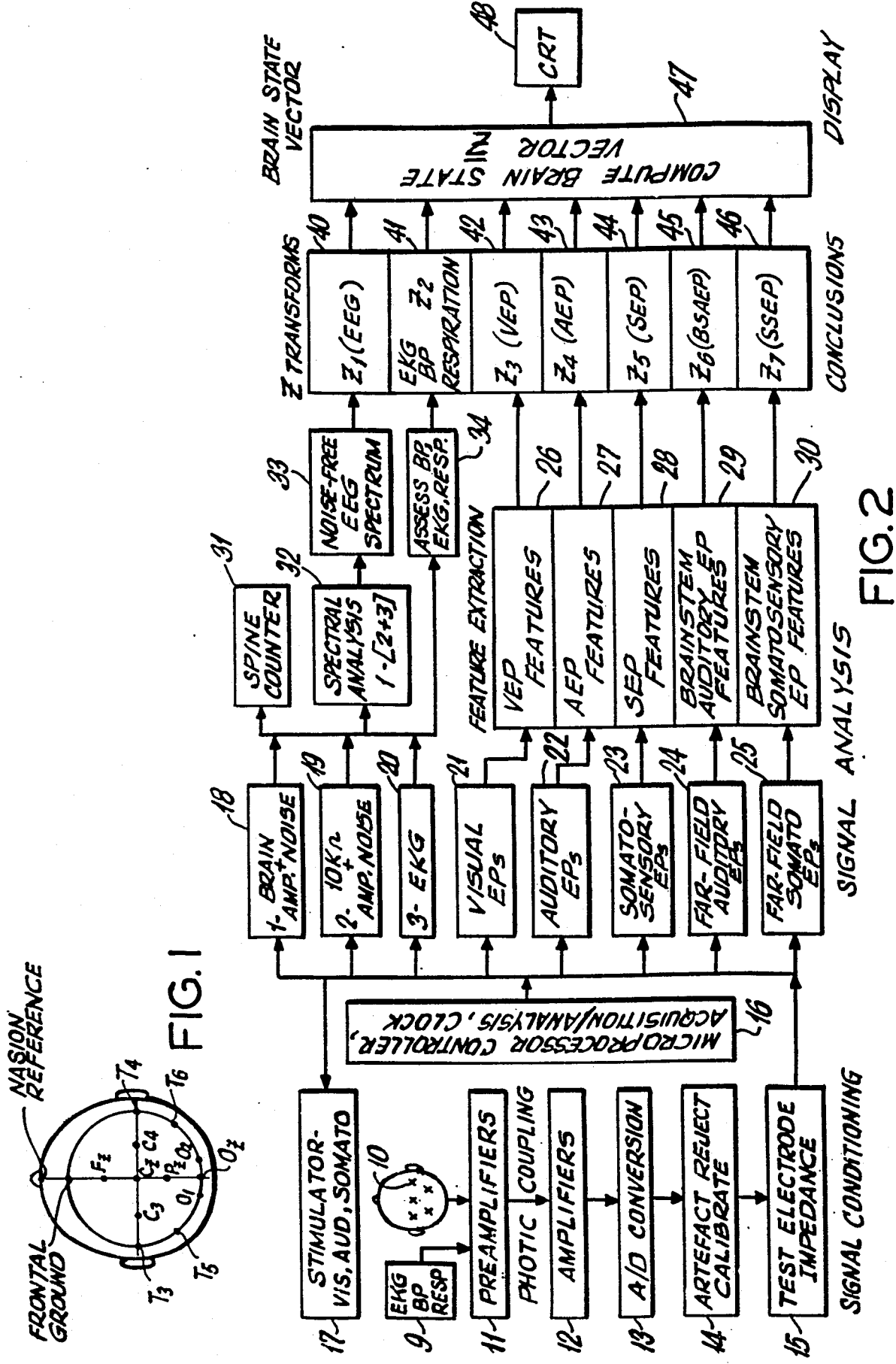

ELECTROENCEPHALOGRAPHIC METHOD AND SYSTEM FOR THE QUANTITATIVE DESCRIPTION OF PATIENT BRAIN STATES

BACKGROUND OF THE INVENTION

The present invention relates to electronic medical instruments and more particularly to an electroencephalograph instrument for the analysis and display of abnormal brain states.

In medicine it is frequently of vital importance to determine the extent and type of a patient's abnormal brain states. For example, when a patient is in a comatose state due to an anesthetic during surgery or other procedures, it may be important to monitor the brain state of the patient to determine if more or less anesthetic is needed, if the anesthetic should be changed, and if the procedure may continue or should be halted or altered. As another example, in hospital intensive care the brain state of a patient, at risk for brain damage for a variety of possible reasons, may be monitored to aid in diagnosis and to determine the optimal level and type of medication or other treatment. In addition, comprehensive quantitative analysis and display of a patient's abnormal brain state may be of vital importance in the differential diagnosis and evaluation of various neurological diseases, assessment and prognosis of head injury victims or discrimination between the so-called "flat EEG" of cerebral death versus the effects of deep barbiturate intoxication.

There is considerable interest and discussion regarding the medical and legal definition of death and its relationship to cerebral death. There has been a considerable amount of publicity regarding the question of whether a comatose patient may be, either for medical or legal purposes, considered or declared dead. This type of question arises in a number of different contexts. For example: Should the use of life support systems be continued for long-term patients in a deep coma? Should organ transplants from comatose patients be permitted and at what stage? and, In the event of limited medical facilities, for example, in an emergency or a battlefield situation, which comatose patients should receive treatment efforts and facilities?

The present inventor, in his prior U.S. Pat. No. 3,706,308 entitled "Life Detecting Medical Instrument", attempted to provide a portable device which would determine the presence or absence of life in a comatose patient. That instrument had certain limitations as to sensitivity; for example, it may not have been able to accurately determine whether a patient was in a deep coma due to barbiturates or had suffered cerebral death. The instrument of the present invention is devised to extend this sensitivity by addition of many additional measures of brain activity, to increase precision by providing separate quantitative indices of the state of different regions of the cortex, thalamus and brain stem, to provide a basis for quantitative prognosis of the outcome as well as differential diagnosis of brain damage or dysfunction, and to provide a multivariate brain state vector (BSV) to facilitate presentation and comprehension of information about the quality, severity and stability of abnormal brain states.

The objective and precise determination of death may be critical for optimal but ethical organ transplants, such as heart transplants. If organ transplantation is to be successful, the organ must be removed as soon as possible after death. If the removal of the heart is delayed, there is a risk that it will be damaged and unusable. The removal of a vital organ precludes any revival of the donor's life. A doctor or hospital may run the risk of civil or even criminal liability if it is later held that a patient was not legally dead at the time the vital organ was removed.

Traditionally, medical science has accepted the classical definition of death as being a total stoppage of the circulation of the blood and a cessation of the animal and vital functions, such as respiration and pulsation. Many physicians now doubt that the traditional definition of death is adequate. A more modern and accepted definition of death is based upon the cessation of brain-wave activity; for example, see Hamlin, Life or Death EEG, 190 J.A.M.A., 1964. Death is defined as occurring when the spontaneous brain electrical activity, which is measurable on an electroencephalograph (EEG), is isopotential or "flat" (without brain waves two microvolts ($2\mu V$) in amplitude) measured by specified amplifiers at specified gain.

Yet, the presence of a flat brain wave is not a reliable indication of the lack of life. Cases have been reported with isopotential EEG and subsequent recovery of the patient, especially after suicidal or accidental ingestion of large doses of barbiturate. Further, the presence of amplifier noise causes decisions about the presence or absence of low amplitude EEG activity to sometimes be equivocal. Even with flat EEG after barbiturate overdoses, the brain may remain electrically reactive to sensory stimulation and recovery can occur.

Neurophysiologists presently employ average response computation to enhance the signal-to-noise ratio of the electrical responses of the brain to sensory stimuli. A series of strong stimuli is delivered to the sensory receptors of the organism and the average evoked response of the brain, or "EP", is examined for transient brain wave reaction phase-locked to the stimulation. Noise is not phase-locked, so that averaging the brain wave activity for a series of stimuli provides an enhancement of signal-related potentials. Since particular sensory systems may be damaged in a given patient, preferably one should test three of the major sensory systems. Presence of a non-zero sensory EP constitutes unequivocal proof of life.

Objectives of the Invention

It is an objective of the present invention to provide a means using an electroencephalographic system for accurately and quantitatively evaluating the states of different regions of the brain, especially in comatose patients after head injury, for the purpose of diagnosis of the locus and extent of damage, prognosis of the duration of coma and probability of permanent impairment of brain functions, and guidance of treatment.

It is an objective of the present invention to provide a means for accurately and quantitatively determining brain states defined relative to a statistical analysis of brain states in patients without brain damage, who are comparable with patients in terms of age.

It is an objective of the present invention to provide a means utilizing an electroencephalographic system for accurately and quantitatively determining a patient's brain state which provides a display which is comprehensible by unspecialized, although trained, medical personnel and does not require the attendance of a trained neurologist.

It is an objective of the present invention to provide a means utilizing an electroenocephalographic system for quantitative and qualitative description of a patient's brain state which utilizes an on-line microprocessor computer based system so that the data may be utilized immediately, for example, for patient monitoring.

It is an objective of the present invention to provide a means utilizing an electroencephalograhic system, for accurately and quantitatively determining a patient's brain state, which is portable so that it may be transported to different areas of a hospital or other health facility and used to monitor patients upon admission, during surgery or intensive care.

It is an objective of the present invention to provide a means utilizing an electroencephalographic system for accurately determining cerebral death and distinguishing it from other comatose states, such as barbiturate induced deep comas, from which the patient may recover.

It is an objective of the present invention to provide a means utilizing an electroencephalographic system for accurately determining brain state or cerebral death which permits, as an alternative, the permanent recording of the electrical activity of the patient's brain to be used for subsequent evaluation or legal evidence.

It is an objective of the present invention to provide a means utilizing an electroencephalographic system for accurately and quantitatively analyzing a patient's brain state which is safe for the patient and which does not present any danger of electrical shocks to the patient when used in conjunction with other equipment in a surgical or intensive care unit.

BRIEF DESCRIPTION OF THE DRAWINGS

Other objectives and features of the present invention will be apparent from the following detailed description which provides the inventor's presently known best mode of practicing the invention. The following detailed description should be taken in conjunction with the accompanying drawings.

In the drawings:

FIG. 1 is a diagrammatic top view of the placement of the electrodes on the patient's head; and FIG. 2 is a block electronic schematic drawing of the system utilized in the present invention.

DETAILED DESCRIPTION OF THE INVENTION

The detection of the patient's brainwaves may be made using conventional electrode placement and conventional fixed-gain low-noise isolated amplifiers. However, preferably the electrode placement and amplifier system described below are utilized.

Preferably the patient's head will be shaved and EEG electrodes located in a web of elastic bands placed on the patient's head. Battery powered FET preamplifiers may be contained in the web to provide initial amplification and a low impedance output to decrease pickup of electrical noise. The electrodes may be of the Beckman (Trademark) type and the bands may be fastened using a plastic hook-eye system of the Velcro (Trademark) type. The electrodes in the elastic bands are located according to the International 10/20 System as they stretch. The bands will retain the relative distances between the electrode locations in approximately the correct ratios, even though the sizes of patients' heads will vary. One band encircles the head and carries electrodes corresponding to 10/20 System positions $T_5$, $O_1$, $O_Z$, $O_2$, $T_6$ and also a frontal ground. A second band stretches from nasion to inion and carries a reference electrode at the nasion, and electrodes at positions corresponding in the 10/20 positions of $F_Z$, $C_Z$ and $P_Z$. A third band goes from the position of $T_3$ to $T_4$ and carries electrodes at positions $C_3$ and $C_4$. An earclip lead is connected to each earlobe and the two earclip leads are linked together as another reference electrode. A third reference electrode (for somatosensory far field EPs) is placed on the knee or hand contralateral to the side of median nerve stimulation. The output of the entire electrode and FET preamplifier array (cable harness) is connected to a single male-female multi-prong type electrical low noise plug, so that it can be rapidly connected or disconnected from the inputs of the EEG amplifiers.

Each of the twelve specifically located electrodes, as shown in FIG. 1, may provide important brain wave analog signals which may be evoked responses to specified stimuli or ongoing EEG activity. The utility of the various electrodes and the brain wave activity that may be expected at those electrodes is as follows: The electrodes $F_Z$ and $P_Z$ will provide samples of EEG and EPs to compound stimuli from the frontal and parietal regions of the cortex; electrodes $C_3$ and $C_4$ will provide EEG and EPs to compound stimuli, particularly somatosensory stimuli, from the central regions of the cortex; electrodes $O_1$ and $O_2$ will provide EEG and EPs to compound stimuli, particularly visual stimuli, from the occipital areas of the cortex; and electrodes $T_3$ and $T_4$ will provide EEG and EPs to compound stimuli, particularly auditory stimuli, from the temporal areas of the cortex. In addition, the electrodes $T_5$ and $T_6$ will give a left and right side location from which to record "far field" or brain stem evoked responses to auditory and somatosensory stimuli. $C_Z$ vertex) and $O_Z$ provide a top and rear location from which to record these brain stem EPs. It is possible that analysis of the EPs simultaneously recorded from these four positions ($T_5$, $T_6$, $C_Z$, $O_Z$) may permit better analysis of the volume distribution of electrical activity within the brain stem and provide an improved estimate of the lateralization of damage. Only some of these electrodes need be used if constrained by the location of cranial injury or the need for surgical access to a head region. For example, unilateral placements can be used on the side opposite the craniotomy.

An additional pair of electrodes is placed transorbitally to monitor eye movements and blinks. Data relating to ongoing EKG, respiration and blood are also obtained using conventional electrode placements and transducers. Samples of "scalp EKG" are obtained from the EEG data on the nasion versus earlobe electrodes.

The automatic "Brain State Analyzer" (BSA) of the present invention is a computer based system utilizing a solid-state electronic microprocessor (one or a series of integrated circuits). The system used low-noise fixed-gain amplifiers, for example, of the type described at page 75 of the inventor's book, *Functional Neuroscience*, Vol. II, "Neurometrics: Clinical Applications of Qualitative Electrophysiology", published 1977 by Lawrence Erlbaum Associates. That book, hereinafter called the "Dr. John text", and particularly its Chapter 4 at pages 75 through 85, is incorporated by reference herein. The input stage of the amplifiers is photically coupled, i.e., a non-conductive transducer coupling, for example, using a light emitting diode (LED) and a photoresponsive diode. This permits absolutely safe operation within the electrical environment of a life support system. The amplifiers are controlled and their output monitored by the microprocessor which also controls the multi-sensory stimulator used to elicit all evoked responses. Battery powered field effect transistors (FET) can be used as preamplifiers for each electrode, to provide a low impedance output which will further reduce pickup of artefactual electrical noise, as well as providing additional electrical isolation.

During all evoked response computations, both on the patient and on volunteers to obtain the data base, the polarity of the lines carrying power to the transducers, i.e., the flashing strobe, the audio click and the somatosensory stimulus, for visual, auditory or somatosensory stimulation are reversed on every alternate stimulus using a solid state switching device. This alternating reversal of transducer power helps reduce or may eliminate stimulus artifact from the records.

As shown in FIG. 2, the electrodes 10 are attached to a signal conditioning data terminal which includes a set of fixed gain preamplifiers 11, with one preamplifier connected to each electrode. The number of fixed gain preamplifiers corresponds to the number of electrodes attached to the head to detect brain waves. In addition, four preamplifiers are connected to electrodes 9 attached to other portions of the subject to detect muscle artifact, electrocardiogram (EKG), blood pressure, and respiration.

The preamplifiers 11 are connected, by photic coupling, to amplifiers 12 which are connected to the analog-to-digital converter 13. There are a number of commercially available variable gain A-D converters suitable for this purpose. Preferably a single A-D converter is used which, in effect, multiplexes each of the channels and digitizes their output in sequence. The A/D conversion 13 is connected to the artifact reject calibrate 14. Preferably the artifact reject calibrate 14 detects and rejects those signals associated with muscle artifact or other movements which would tend to distort the brain wave information. Such movement may be due to movement of hospital personnel in proximity to the patient or involuntary muscle movement of a patient. Such artifacts are characterized by large rapid signals and may be eliminated by a set of predetermined maximum threshold value which, if exceeded, indicate the presence of such artifact. Preferably the artifact reject 14 will simply suppress or cancel out the signal during the time it is receiving the signals in excess of the predetermined threshold.

The impedances of the electrodes are automatically tested by automatic impedance testing means 15 to insure that there is a good contact between the scalp of the subject and the electrode. Generally it is preferable that the impedance be below 5000 ohms at each electrode. If the impedance exceeds a predetermined level, for example, 50,000 ohms, the signals from that electrode may be blanked out, i.e., not recorded, and the technician informed by an alerting signal.

The microprocessor controller 16 provides a program control for the stimulator 17 and performs the signal analysis. Details on certain portions of the system, particularly the stimulator 17, may be found in the Dr. John text at Chapter 4, pages 75 through 85.

The stimulator 17 includes a strobe light flash above the patient and, in addition, an audio amplifier connected to earphones on the patient's ears. The somatostimulator may be electrodes which give a slight electrical shock through an isolation circuit. The stimulator 17 provides a programmed set of stimuli to the patient, such as a series of flashes, a series of clicks, and a series of slight shocks. The stimulator is controlled by the microprocessor whose programming, when it is acquiring brain wave information from the patient, may be obtained from a ROM (read only memory) or a programmed magnetic disk or a programmed magnetic tape cartridge or magnetic tape system.

The microprocessor controller 16 is connected to each of the electronic subcircuits 18 through 25. The subcircuits "Brain and Amplifier Noise 18" and "Resistor and Amplifier Noise 19" are used to separate the ongoing brain activity from the noise found in the amplifiers and the preamplifiers 11 and 12 respectively. The electrocardiogram electrodes, connected to the patient to detect the patient's heartbeat, are connected to EKG subcircuit 20. The patient's brain waves evoked by the visual stimulator are used to compute the visual EPs in the microprocessor, stored in the memory sector for Visual EPs 21, the patient's auditory responses are similarly computed and stored in the memory sector for auditory EPs 22 and the patient's somatosensory responses are similarly computed and stored in the memory sector for somatosensory EPs 21. The patient's far field auditory EPs (AEP) are computed and stored in far-field auditory EP memory sector 24 and the patient's far field somatic EPs are computed and stored in memory sector 25. Those evoked responses are described in greater detail subsequently. At each latency point along the analysis epoch of each EP thus computed, the standard deviation or variance is also computed as described in Dr. John's text.

The signal analysis portion of the system also includes software for extraction of features of the EPs which are diagnostically useful. The visual evoked response (VEP) features 26, the auditory evoked response (AEP) features 27 and the somatosensory evoked response (SEP) features 28 are extracted by this software and stored in suitable memory devices, for example, a random access memory of a "scratch-pad" type of memory for on-line computational purposes. Similarly, the brain stem auditory features 29 are extracted from the far field auditory EPs 24 and the brain wave somatosensory EP features 30 are extracted from the far field somatosensory EPs 25.

In addition, spoke software counter 31 counts the number of electrical excursions 30 to 80 mg in duration which exceed predetermined limits of rise (2 $\mu$V/mS), amplitude (50 $\mu$V) and fall (2 $\mu$V/mS) which occur in each electrode channel (possible epileptiform spikes). These numbers are stored and displayed upon request. A buffer sector of memory may be used by the spike counter subroutines to store waveshapes identified as spikes for subsequent visual display. Software subroutines for spectral analysis 32 are used to separate the spectrum of the electrical activity of the brain from the amplifier noise, which may be of equal or greater energy as the EEG comes close to being "flat". The power spectrum of the 10 K ohms resistors plus amplifier noise from subcircuit 19 and the power spectrum of the EKG signal from EKG subcircuit 20 are computed by the spectral analysis subroutines 32 and subtracted from the power spectrum of the brain electrical activity plus amplifier noise from subcircuit 18. This produces a noise-free EEG spectrum 33, purified of possible contamination by low-level EKG potentials. Other software subroutines 34 extract information about amplitude and rate to provide a separate assessment of blood pressure (BP), EKG and respiration 34.

Each of the foregoing extracted features then undergoes a Z-transformation. The set of Z-transformations, as computed by the subroutines 40 through 46, are then used to compute a vector sum $\Sigma$ to form a brain state vector (BSV) 47. The brain state vector is displayed on a cathode ray tube (CRT) 18, although other types of display devices may alternatively be used.

Note that special purpose computer or hybrid circuits might be constructed to replace any or all of the above subroutines.

Average responses can be computed by special purpose hardware or by appropriate software routines in a general purpose computing device. Average response computation provides a useful way to extract the response of the brain to sensory stimulation despite background noise, for example, "white", i.e., random Gaussian, noise arising from the amplifier and ongoing electrical activity of the brain not related to the sensory stimulation. Average evoked responses can be revealed by an average response computer even when visual inspection by a trained neurophysiologist reveals no response to the stimulus in the ongoing EEG display or on an oscilloscope. Electrical responses evoked in the brain by presentation of sensory stimuli may be undistinguishable from the other electrical activity of the brain, when viewed on an oscilloscope or on a conventional EEG paper record.

In signal averaging, the computer calculates the average voltage $$\frac{\Sigma V(t_i)}{N}$$

of the electrical response to the stimulus ("signal") plus the unrelated electrical activity of the brain ("noise") at each of a series of time points $t_1, t_2 \ldots, t_n$, after the presentation of each of a sequence of N stimuli. Since the electrical response of the brain to the stimulus will be phase-locked to the time of stimulation, the time course of brain voltages related to the signal will be reproducible across successive presentations and that average voltage at each time point will converge to the value of the evoked response at the corresponding latency. Since the electrical activity of the brain unrelated to the stimulus, as well as electrical noise arising from the instrumentation or ambient sources, will be in random phase relationship to the time of stimulation, the time course of brain voltages unrelated to the signal will be random across successive presentations. Thus, the average value of the voltage at each time point not related to the signal will converge to zero. Since the shape of the signal will be relatively invariant as long as the state of the nervous system remains stationary, the average evoked response waveshape provides a reliable reflection of the state of the brain. Successive components of these evoked response waveshapes correspond to the activity of different neural subsystems in the brain and thus provide information about the functional status of different anatomical regions. Further details are to be found in Dr. John's text.

The extracted EP waveshapes are analyzed as shown in FIG. 2. The EP data (visual EPs 21, auditory EPs 22, somatosensory EPs 23, far field auditory EPs 24, far field somatosensory EPs 25) are further reduced by extracting specific features (neurometric indices) corresponding to diagnostically useful characteristics such as component amplitude and latency, bilateral symmetry and waveshape morphology.

The neurometric features extracted from the data are then subjected to Z-transformation. That is, for each feature the differences between the individual value and the mean for the non-brain trauma control group for that age group is divided by the standard deviation of the non-brain trauma control group, producing the Z-transforms. The Z-transformation method (Parl, B., *Basic Statistics*, pages 165–166) characterizes the deviation of the subject value from the control value as a number of standard deviations or "error steps".

The formula is:

$$Z = \frac{X - M}{\sigma x}$$

where the number of error steps, Z, is representative of a particular neurometric invariate or multivariate index (in this case a feature) and equal to the difference between the patient's index value for that feature, X, and the group mean value, M, divided by the standard deviation of the whole sample, $\sigma_x$. The total sample standard deviation is computed according to:

$$\sigma_x = \sqrt{\Sigma (x - \bar{x})^2}$$

where x is the patient index value and $\bar{x}$ is the average index value of the control group, i.e., the group of non-brain trauma persons of the corresponding age.

The effect of the Z-transform is to provide the common metric of relative probability as the dimensions or units in which all features are stated. Relative probability here means the probability of obtaining the observed value by chance in a member of the non-brain trauma population.

The neurometric features (EEG 40, EKP-BP-Respiration 41, VEP 42, AEP 43, SEP 44, BSAEP 45, BSSEP 46) are thus computed and expressed in this common metric of relative probability. Thus, it becomes possible to construct a brain state vector, $\bar{Z}$, for any selected combination of i features, where $\bar{Z} = \sqrt{a^{z_1^2} + a^{z_2^2} + a^{z_3^2} = \ldots + a^{z_i^2}}$. Usually, the i selected features will be those neutrometric indices thus obtained which are improbable to observe in a normal population, where the Z-value considered improbable can be selected according to the criteria most appropriate to the specific application under consideration. The length of the brain state vector $\bar{Z}$ reflects the extent of the patient's brain damage in multivariate (multifeature) terms, while the orientation of $\bar{Z}$ reflects the nature of the damage. The vector $\bar{Z}$, which is the Brain State Vector (BSV) is then displayed, preferably on a CRT (cathode ray tube) and preferably in conjunction with an associated memory to show changes in the BSV over time. Such a display can show both length and orientation information. Such CRT tubes are commercially available. The associated memory may be a portion of the magnetic disk memory having read-write capability.

The entire brain state analyzer (BSA) system, comprising amplifiers, stimulators, microprocessor, magnetic storage devices for permanent records (if desired) and the video terminal used for graphic and alphanumeric displays and interactive system operation, is preferably compactly mounted on a portable cart with rubber casters.

After the electrodes are placed on the patient, the BSA system will automatically test the impedance of each electrode and calibrate each amplifier. Provision for regular repetition of such impedance and calibration measures throughout extended periods of observation is preferably incorporated into the BSA software. Unacceptable impedance or calibration values in any channel will be brought to the attention of the operator by a warning system. In addition, preferably, muscle artifact of the patient, for example, involuntary motion associated with eye movement, is detected and used to control the suppression of data acquisition, or the data record, during such muscle artifact. Further details concerning a suitable impedance testing and an artifact suppression system may be found in the Dr. John test at pages 76, 78, respectively.

The baseline data may be gathered using a group of volunteers or patients who are candidates for elective surgery, for conditions with no implications for brain function and without a previously history of head trauma or neurological disease. In accordance with hospital, university or governmental guidelines, the measurement procedures and the purpose of the project will be explained to volunteers and patients who would constitute acceptable members of such a control group, and informed consent forms will be signed by those who agree to serve as volunteers. One such group will be run at each of several ages, to establish age-dependence of brain state vector BSV component measures explained below.

From each of these volunteer subjects, four kinds of data will be obtained: (a) resting EEG; (b) average evoked responses (EPs) to simultaneous stimulation, for example, 120 stimuli, presented at random intervals with an average interval of one second, with bright flashes delivered by an overhead strobe while the patient's eyes are shut plus a 75 dB click delivered using earphones to both ears, plus a somatosensory stimulus (see below); (c) "far field" responses to 75 dB clicks delivered alternately to the left and right ear by means of the earphones at a rate of 20/s for 4 minutes (2400 clicks to each ear); (d) "far field" responses to 0.2 ms electrical pulses delivered at a frequency of 10/S alternately to the left and right median nerves using two silver disk electrodes placed over the skin at the wrist with the cathode located proximal to the wrist. The stimulating position will be selected to give a thumb twitch at the lowest stimulation current (about 6–8mA). All electrical stimuli are delivered using electrically isolated photic coupled constant current stimulators to guarantee complete electrical isolation.

The resulting norms, obtained from groups of brain-normal subjects and grouped by appropriate age ranges, constitute the means and standard deviations for Z-transformation of each measure to be included in the BSV. Where these measures change as a function of age, Z transform will be made relative to the norms corresponding to the age of the patient. The full set of norms will be stored in the BSA microprocessor memory, so Z transformation can be accomplished on-line immediately after data analysis, as described further below. However, before these normative data are entered into the BSA memory, they would have been compared with existing normative data in the literature to establish that the parameters and design decisions incorporated into the BSA produce measurements of individual components of the BSV like those already published in the literature by investigators studying one or another of these various aspects of brain electrical response.

If the BSA is to be used as an anesthesia monitor or controller, a normative control group (anesthetic control group) of at least 20 individuals must be used to provide adequate baseline data for each anesthetic agent with which the BSA will be used. In other words, different anesthetic agents may produce different sets of norms (normal neurometric features) for brain-normal subjects. These patients would be volunteers who are to undergo anesthesia for elective surgery for conditions with no implications for brain function. The anesthetic and other medications or procedures in each anesthetic control group corresponds to those conditions under which the BSA is used to monitor that anesthetic. Anesthesia would be administered by a well qualified anesthesiologist who will try to keep the members of the control group at as comparable a stage of anesthesia as current methods permit.

For each of the spectral analysis features, the mean value and standard deviation is computed separately for 24 two and one-half second samples of spontaneous EEG and 24 two and one-half second samples of environmental noise. First, each of the spectral analysis features computed from the simultaneously recorded "scalp EKG" channel will be tested against the corresponding measures from each EEG lead, using Students 't'-test. All leads for which this test shows no significant difference will be considered as only EKG artifact, i.e., "no brain activity present." For all remaining leads, the values of features obtained by spectral analysis of the "scalp EKG" will be subtracted from those obtained by spectral analysis of the spontaneous EEG. The resulting set of features has thus been "purified" of contamination by scalp EKG, a major problem when evaluating low amplitude EEGs.

Each of the corrected EEG features (purified of scalp EKG) will be compared with the corresponding measures obtained by spectral analysis of the "environmental noise" samples, using the 't'-test. Data from all channels for which this test shows no significant difference will be considered as only amplifier noise, i.e., "no biological activity present". For all remaining measures, the values obtained by analysis of environmental noise will be subtracted from those obtained by analysis of the spontaneous EEG. The resulting set of measures has been "purified" of contamination by environmental noise, including the noise level of the EEG amplifiers themselves, as well as by scalp EKG, and represents a good estimate of the electrical activity of the regions of brain monitored by each electrode.

The elaborate data purification steps set forth above will also be used to obtain baseline data from the control subjects or anesthesia baseline patients. These data purification steps are especially important after the indiction of barbiturate anesthesia, with the consequent lowering of the patient's EEG amplitudes toward the amplifier noise levels. In the case of patients with head trauma, in whom intervention may include barbituration to the depth where the EEG becomes "isopotential" by visual inspection, the proposed purification procedure is essential in order to detect any low-level EEG activity imbedded in the amplifier noise.

Only those EEG measures which survive after this purification procedure can contribute usefully to construction of the BSV for a head trauma patient during intervention.

The data for the patient's ongoing EEG activity and evoked responses provided an over-abundance of digital data and much of that data is mingled with various types of noise. One must separate the data from the noise and then separate the meaningful data from that which is less useful. First, the data, as explained above, must be "purified", i.e., any brain wave data must be separated from electrical waves arising from other causes, for example, amplifier noise, muscle artifact, environmental noise, and scalp EKG. Secondly, the Z-transformed features must be found to be significant, i.e., statistically improbable in brain-normal subjects. Thirdly, only the subsets of features ("State features", described later) which have been found by an extensive testing program to be most parsimonious and most diagnostically useful for particular purposes (best discriminate abnormal states from normal), should be utilized. The most meaningful features for one condition may differ from those for another. For example, two different anesthetics may affect two different sets of brain state features.

Data Analysis and Reduction Methods

The following is an example of the type of ongoing EEG data which is gathered and analyzed by the present invention. It will be understood, however, that as experience is accumulated and literature is published on these matters, the data that is gathered may be desirable to be changed. The preferred resting EEG data consists of twenty-four 2.5 second artifact-free segments of spontaneous EEG (without stimuli from the system). Optionally, a smaller number of longer EEG segments may be used to achieve better sensitivity to frequencies in the delta bond. These data are recorded (accumulated) with the head electrodes electrically referenced to the linked earlobe. Each segment of acceptable data is followed by a 2.5 second sample of "environmental noise" which may be obtained by a programmed switching of an automatic circuit which disconnects all EEG leads from the amplifier inputs and replaces those leads with 10 K resistive "dummy loads". The environmental noise is the electrical activity detected while the amplifiers are connected to the dummy loads. During the first procedure, one channel is connected to nasion versus earlobe, to detect EKG activity reflected at the scalp.

For each EEG electrode and for the "scalp EKG", spectral analyses are computed separately for each of the 48 data segments, and the resulting spectral densities are expressed as absolute and relative (%) power in delta, theta, alpha and beta bands. Average coherence and amplitude symmetry are also computed separately for each band for each pair of homologous electrodes. Spectral analyses, coherence and symmetry may be computed by digital filters or using analog circuits.

The following examples of the analysis of evoked response data is given by way of example to show the type of program that may be employed, although other such programs may alternatively be used. For example, the number and timing of the stimuli may be changed to accord with future developments in the EP field.

Compound (simultaneous) visual, auditory and somatosensory stimuli at a repetition rate of 1/sec are presented to the patient to give 120 evoked responses. For each electrode two average evoked responses are computed using a 500 ms analysis epoch, one from the odd- and the other from the even-numbered stimuli. The variance of these two average EPs is also computed. These two average EPs permit a test of split-half reliability, which is one important way to establish the presence of a low amplitude EP. The two averages are cross-correlated and the correlation coefficients are log-transformed to assess waveshape similarity across the whole analysis epoch. The significance of the difference between the split halves of the sample is also assessed by 't'-test at each time point along the analysis epoch. Z-transforms of these indices establish the probability that a true evoked response has been elicited in the corresponding electrode. Similarly, the signal-to-noise ratio of each of the split halves and of the combined full sample is computed at each latency point in the analysis epoch. The S/N value is Z-transformed relative to the mean and variance of a sample of 120 segments of spontaneous EEG, i.e., in the absence of the compound stimuli, selected at randomized intervals from the same patient with an average interval of one second, each segment lasting 500 ms. These Z-transformed S/N values provide an independent estimate of the probability that a real evoked response, and not noise, has been elicited. Any electrode showing the presence of evoked potentials under any of these tests is considered to establish the presence of brain activity.

For all electrodes in which those tests indicate the presence of a real evoked response, response features are extracted. The response features include the value of the average response at each 10 ms along the 500 ms analysis epoch, the variance at each time point, the S/N at each time point, the amplitude and latency of each positive and negative peak, the asymmetry of energy and of latency and the cross-correlation between waveshapes from homologous electrode derivations. The significance of any asymmetry between EPs from homologous leads is assessed by the 't'-test at each latency point. These features, after Z-transform, summarize the major aspects of the EP waveshapes from each lead or pair of symmetrical leads.

The analysis of "Far-Field" Auditory Evoked Responses (FFAER) uses data from the electrodes $C_z$, $O_z$, $T_5$ and $T_6$. The patient's responses to alternate clicks are averaged, yielding far-field EPs for 2400 stimuli delivered at the rate of 20/sec in alternation to the left and right ears by earphones. A 10 ms analysis epoch is used. If desirable, and using an additional, and not shown, electrostatic matrix printer device, the topography of the potential fields of each component of the average EPs to left and right ear stimulation can be mapped, using methods analogous to those published by Vaughan or Lehmann. Using the methods of the present invention, the salient features of these EPs are extracted and Z-transformed, separately for left ear and right ear stimulation. These EPs to unilateral stimuli reflect the state of the lateral lemniscal pathways on each side of the brain stem. Since each component of the "far-field" auditory EP has been identified as corresponding to the activity of a particular brain stem region, such analyses provide a relatively specific estimate of the state of different regions or structures in the brain stem. Changes in component latency or amplitude reflect damage at corresponding anatomical levels.

To obtain "Far-Field" Somatosensory Evoked Responses (FFSER) the somatosensory evoked responses are analyzed analogous to the treatment of auditory far-field responses, but separate analyses are performed for responses to left and right wrist stimulation. The analysis of these EPs reflect the state of medial lemniscal pathways on each side of the brain stem.

Dimensionality of the Brain State Vector

To obtain the normative data from subjects without brain wave abnormality and to define the dimensionality of the brain state vector, the same type of analyses described above must be carried out on a group of 20 normal subjects of the same age. More specifically, for each subject of the control group a set of Z-transformed features is extracted from the spontaneous EEG, cortical EPs to compound stimuli, and far-field responses to auditory and to somatosensory stimuli delivered to the left and right sides. Responses not statistically significantly above the noise level are eliminated, leaving a set of responses recorded from a variety of electrodes, which truly reflect the brain activity of normal subjects. Since there is a great deal of data redundancy between different electrode placements and between different features extracted from the spontaneous or evoked activity, this set of features must be subjected to factor analysis using the data from control subjects. A Varimax rotation (rotations of sets of factors, treated as axes, each of which accounts for energy, i.e., spans the measured space and which yields orientations of axes best corresponding to physiological processes) should be used, as described in the Dr. John text at page 60.

The results of the factor analysis of normal subjects establishes the dimensionality of the full set of measurements obtained from the BSA. These dimensions, i.e., these factors important (best able to discrminate) by factor analysis, describe the state of various cortical regions reflected in EEG measures, the state of sensory-specific pathways and thalamic nuclei and primary cortical receiving areas assessed by short-latency components of the compound EP, the state of non-sensory-specific pathways and thalamic muclei and association cortex assessed by long-latency components of the compound EP, the state of lateral lemniscal pathways in the brain stem assessed by far-field auditory EPs and medical lemniscal pathways in the brain stem assessed by far-field somatosensory EPs.

The dimensionality (the number of factors which account for a specified percentage of the energy of the original analog brain wave shapes) of the brain state vector (BSV) is taken to be the number of factors necessary to account for 95% of the measure space. For each such dimension (factor), that feature in the measure set which receives the highest loading from that factor is taken as the best estimate of that dimension of brain state in the measure set, provided that the loading is above 0.90. If no single feature receives a loading of 0.90 (81% of variance accounted for), then the two features receiving the highest loadings above 0.7 must be selected. Factors for which no feature receives a loading above 0.7 should be discarded from the state dimensions, i.e., not used. Those features that load above 0.7 are referred to as state features. The set of state features thus obtained is the subgroup of neurometric indices which describes brain states with the most parsimonious measurements in the most complete way. Those measurements of brain activity which do not belong to the set of state features defined in this way are either insensitive to brain state or redundant, and should be dropped from the measure set, since they constitute a source of error variance but provide little additional information.

Construction of the Brain State Vector

The vector sum of the Z-transformed state features constitutes the BSV. The BSV has the dimensionality revealed by factor analysis of the full set of available measures of brain electrical activity, both spontaneous and evoked from cortex and brain stem. For each dimension (state feature), the BSV has a magnitude inversely related to the probability of that state feature in a subject without brain damage. A threshold is set such that Z-values significant at less than the 0.01 level are set equal to zero.

Thus, the BSV in a patient whose state features are all within the normal range will be of zero magnitude (zero length) except for random variations. As state features become increasingly abnormal, the Z-transform of those features exceed significance at the 0.01 level and the BSV magnitude, $\overline{Z}$, is equal to the square root of the sum of the significant state feature Z-values squared, divided by the number of features:

$$\overline{Z} = \sqrt{\frac{Z^2 + Z_2^2 + \ldots + Z_n^2}{n}}$$

The nature of the brain dysfunctions in the patient can be identified by the anatomical/functional correlates of the measures represented by each subscript of $Z_i^2$ in the equation above, since each of these variables was significantly abnormal. If desired, separate BSV's can be computed to describe the state of the cortex, the thalamine and the brain stem. It may be advantageous to compute such anatomically distinct BSV's in certain cases where damage or dysfunction has been found to be localized to one anatomical level, or where treatments may be expected to affect brain structures on one level. Thus, one could construct a Brain State Vector, a Cortical State Bector, a Thalamic State Vector, or a Brain Stem State Vector.

The BSA may be used in an environment, such as a hospital intensive care unit, where personnel are busily engaged in complex activities. Data presentation on a CRT (cathode ray tube) permits options of the amount and type of information desired by the user, which will vary from circumstance to circumstance. For example, in some cases it may be desirable to display the full Brain State Vector, while in other cases only the "Brain Stem Vector" is of interest. The most basic information is the length of the BSV and its rate of change with time (first derivative). This tells at a glance how bad or good the patient's brain state might be, and could be a digital number or an intensified portion of a line segment. Display of a series of numbers representing successive BSV measures on the same patient, or a series of lines one below the other showing the length of the BSV and change in length across time, can provide this information at a glance. For example, a historical record may be shown on a memory CRT by lines representing BSV's computed at regular time intervals (10 minutes) and the lines retained on the screen for the selected memory period. The series of lines would describe the development of the patient's condition.

Interrogation of the BSA by typing the number of any variable of interest on the keyboard replaces the BSV display by the Z-value of the requested variables. Hitting the space bar would display the raw waveshape of the measure (e.g., EEG from some region, EP from some region to some stimulus, EKG, etc.) considered beyond normal limits, plus its Z-value. This display is updated every time the BSA cycles through the BSV computation, which is continuously repeated while the patient is being monitored. Up to 4 variables considered of critical interest may be graphically displayed simultaneously in this way, together with their individual Z-values and the BSV value ($\overline{Z}$). Hitting the space bar again returns the display to the simplified tracking mode. A printer may be used to provide hard copy (a printed record) of all measures, in case a permanent record is desired, and the date and time may automatically be recorded on such hard copy.

What is claimed is:

1. The method of determining the brain state of a patient including the steps of:
   (a) attaching a plurality of electrodes to the scalp of a comatose patient or a patient with other brain dysfunctions to detect the patient's brainwaves in the form of electroencephalographic (EEG) and evoked response (EP) data;
   (b) amplifying the electrical signals detected at each electrode;
   (c) using a programmed computer based system as the control for stimulating the patient with a series of multi-sensory stimulations to elicit evoked responses from cortex and brain stem;
   (d) obtaining and analyzing on-line digital EEG or EP data by connecting analog-digital converters to each amplifier, and digitizing all data as it is gathered;
   (e) obtaining sets of on-going EEG and average evoked response data for the patient and using said computer based system to extract diagnostically useful features from such sets of data, and automatic construction of a Z-transform for each such feature based upon a comparison with stored normative data obtained by computing mean values and standard deviations for each feature from groups of subjects or patients without head trauma or brain dysfunction;
   (f) computing a state vector for the patient comprising a vector sum based upon those Z-transformed features which are significantly deviant from normative values; and
   (g) visually displaying the length (severity), orientation (quality) and change with time of said state vector.

2. The method of determining the brain state of claim 1 wherein after the step of digitizing all data as it is gathered the digitized data is examined in a buffer to automatically reject that data which is contaminated by artifacts and then storing the valid (artifact free) data.

3. The method of determining brain state of claim 2 wherein said data are reduced by a spectral analysis of spontaneous EEG and computation of average evoked responses to each type of stimulus.

4. The method of determining brain state of claim 1 wherein said state vector is selected from the group consisting of the brain state vector (BSV), the cortex state vector, the thalamus state vector and the brain stem state vector.

5. The method of determining brain state of claim 1 and including EKG artifact reduction due to scalp EKG by the steps of testing, using the "t" test, the spectral analysis of features from each electrode against the simultaneously measured and similarly computed data from a scalp EKG electrode.

6. The method of determining brain state of claim 5 and including the step, after such EKG artifact reduction, of using the "t" test to compare the data of the features obtained free of scalp EKG with the corresponding measures of environment noise samples.

7. The method of determining brain state of claim 6 wherein said method is used to test patients whose level of barbituration may be to the depth of their showing an isopotential EEG by visual inspection.

8. The method of determining brain state of claim 1 and including the step of automatically, under programmed control, switching EEG electrodes from the amplifier inputs to dummy loads to obtain measures of environmental noise.

9. The method of determining brain state of claim 1 wherein the electrodes are internal to bands and the bands are stretched over the patient's head and an ear-clip electrode is connected to the patient's earlobe.

10. The method of determining brain state of claim 1 and the additional steps of automatically, under control of said computer system, regularly testing the impedance of the electrodes to determine if the impedance at each electrode is within predetermined acceptable limits.

11. The method of determining brain state of claim 1 wherein the stimuli presented to the patient includes, at random intervals, auditory clicks delivered through earphones on the patient and light flashes and somatosensory stimulus.

12. The method of determining brain state of claim 11 wherein the somatosensory stimuli are electrical shock pulses delivered through electrodes removably attached to the patient's wrists or ankles.

13. The method of determining brain state of claim 1 and including the further step of halting the collection of patient EEG data during muscle artifact.

14. The method of determining brain state of claim 1 wherein said visual display is on a cathode ray tube (CRT).

15. A system for determining the brain state of a patient including:
   (a) a plurality of electrodes adapted to be attached to the scalp of a comatose patient or a patient with other brain dysfunctions to detect the patient's brainwaves in the form of electroencephalograph (EEG) and evoked response (EP) data;
   (b) preamplifiers;
   (c) a stimulator means for stimulating the patient in a series of multi-sensory stimulations and stimulations of separate modalities to elicit evoked responses;
   (d) a programmed computer based system means for the control of said stimulator means, including the use of microprocessors for such purposes;
   (e) analog-digital converter means connected to said amplifier means for obtaining on-line digital EEG and EP data;
   (f) means for obtaining sets of on-going EEG and average evoked response data for the patient and automatically constructing a Z-transform for each analytic measure extracted from such sets of data based upon a comparison with normative data from groups of patients without head trauma or other brain dysfunctions;
   (g) means for computing a state vector for the patient comprising a vector sum based upon those Z-transformed features significantly deviant from the normative data; and (h) means for visually displaying the length and change of time of said state vector.

16. The system for determining brain state of claim 15 wherein said preamplifiers include FETs (field effect transistors) positioned closely adjacent said electrodes to reduce artifact pickup by providing a low impedance signal amplifier.

17. The system for determining brain state of claim 15 and further including means photically coupled to said amplifiers to permit said amplification with total safety even in the complex electrical environment of a hospital intensive care unit.

18. The system for determining brain state of claim 15 and further including switching means to switch said system and its display means from the display of the brain state vector (BSV) for the whole brain to the display of particular anatomical regions selected from the group of the cortex, thalamus and brain stem regions.

19. The system of determining brain state of claim 15 and further including bands which are stretched over the patient's head and an earclip electrode which is connected to the patient's earlobe, wherein the said electrodes are internal to the said bands.

20. The system of determining brain state of claim 15 and means for automatically, under control of said computer system, regularly testing the impedance of the electrodes to determine if the impedance at each electrode is within predetermined acceptable limits.

21. The system of determining brain state of claim 15 wherein the stimulator means includes means for presenting, at random intervals, auditory clicks delivered through earphones and light flashes and somatosensory slight electrical shocks.

22. The system of determining brain state of claim 15 wherein the somatosensory stimulus are electrical shock pulses delivered through electrodes removably attached to the patient's wrists or ankles.

23. The system of determining brain state of claim 15 wherein said visual display is on a cathode ray tube (CRT).

* * * * *

UNITED STATES PATENT OFFICE
CERTIFICATE OF CORRECTION

Patent No. 4,201,224   Dated May 6, 1980

Inventor(s) E. Roy John

It is certified that error appears in the above-identified patent and that said Letters Patent are hereby corrected as shown below:

Column 4, line 36 - parenthesis should be inserted before "vertex" (vertex);

Column 4, line 58 - "used" should be --uses--;

Column 8, line 25 - equation should read: $\sigma_x = \sqrt{\Sigma(x - \bar{x})^2}$ Column 8, line 52 - "$\hat{z}$" should read -- $\bar{z}$ --

Column 9, line 13 - "test" should be --text--;

Column 12, line 20 - "eliciated" should be --elicited--;

Signed and Sealed this

Fourteenth Day of October 1980

[SEAL]

Attest:

SIDNEY A. DIAMOND

Attesting Officer    Commissioner of Patents and Trademarks